United States Patent [19]

Strunk et al.

[11] Patent Number: 4,785,108
[45] Date of Patent: Nov. 15, 1988

[54] SUBSTITUTED OXIME CARBAMATES

[75] Inventors: Richard J. Strunk, Cheshire; Richard C. Moore, Wallingford, both of Conn.

[73] Assignee: Uniroyal Chemical Company, Inc., Middlebury, Conn.

[21] Appl. No.: 921,938

[22] Filed: Oct. 21, 1986

Related U.S. Application Data

[60] Division of Ser. No. 616,994, Jun. 4, 1984, Pat. No. 4,640,927, which is a continuation-in-part of Ser. No. 595,156, Mar. 30, 1984, abandoned.

[51] Int. Cl.$^4$ .................. C07D 239/72; C07D 333/72
[52] U.S. Cl. .................................. 546/283; 546/284; 549/75; 549/59; 549/60
[58] Field of Search .......................... 549/75, 59, 60; 546/283, 284

[56] References Cited

U.S. PATENT DOCUMENTS

| | | | |
|---|---|---|---|
| 3,223,585 | 12/1965 | Addor | 167/33 |
| 3,632,621 | 1/1972 | Addor et al. | 260/453 |
| 3,681,386 | 8/1972 | Fridinger et al. | 260/327 |
| 3,755,364 | 8/1973 | Magee | 260/327 |
| 3,832,400 | 8/1974 | Meyer et al. | 260/566 |
| 3,875,232 | 4/1975 | Magee | 260/566 |
| 3,903,289 | 9/1975 | Magee | 424/275 |
| 4,028,413 | 6/1977 | Magee | 260/566 |
| 4,118,389 | 10/1978 | Magee | 260/294.8 |
| 4,128,581 | 12/1978 | Magee | 260/566 |
| 4,215,075 | 7/1980 | Magee | 260/566 |
| 4,640,927 | 2/1987 | Strunk et al. | 514/342 |

FOREIGN PATENT DOCUMENTS

| | | | |
|---|---|---|---|
| 0245835 | 11/1987 | European Pat. Off. | 549/75 |
| 958631 | 5/1964 | United Kingdom . | |
| 1024644 | 3/1966 | United Kingdom | 549/70 |

OTHER PUBLICATIONS

Strunk et al., Chem. Abst., vol. 104 (1986), 168355j.

*Primary Examiner*—Alan Siegel
*Attorney, Agent, or Firm*—William E. Dickheiser

[57] ABSTRACT

A compound having the formula

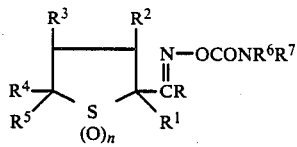

wherein R is $C_1$-$C_4$ alkyl, cyclopropyl, $C_2$-$C_4$ alkoxyalkyl, $C_4$-$C_8$ diakylaminoalkyl, $C_2$-$C_4$ alkylthioalkyl, $C_2$-$C_4$ alkylsulfinylalkyl, $C_2$-$C_4$ alkylsulfonylalkyl, phenyl, $C_7$-$C_9$ aralkyl, $C_7$-$C_9$ alkaryl, furyl, thienyl or pyridyl; $R^1$ is hydrogen or $C_1$-$C_4$ alkyl; $R^2$ is hydrogen or $C_1$-$C_4$ alkyl; $R^3$, $R^4$ and $R^5$ are the same or different and are hydrogen or $C_1$-$C_4$ alkyl; $R^6$ and $R^7$ are the same or different and are hydrogen, $C_1$-$C_4$ alkyl, allyl, benzyl or tolyl with the proviso that both $R^6$ and $R^7$ are not hydrogen; and n is 0, 1 or 2 and methods of making same are disclosed. This compound is useful as a pesticide.

Intermediates useful in synthesizing this pesticidally effective compound are also taught. These intermediate compounds have the structural formulas

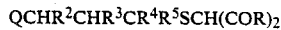

$$QCHR^2CHR^3CR^4R^5SCH(COR)_2$$

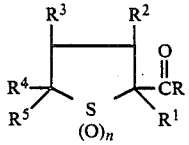

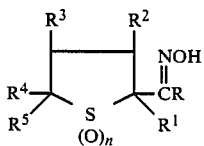

wherein R, $R^1$, $R^2$, $R^3$, $R^4$, and $R^5$ and n have the same meanings as the pesticidally effective compound recited above; and Q is a leaving group. Methods of making these intermediate compounds are described.

3 Claims, No Drawings

SUBSTITUTED OXIME CARBAMATES

CROSS-REFERENCE TO RELATED APPLICATION

This is a division of application Ser. No. 616,994 filed June 4, 1984, now U.S. Pat. No. 4,640,927, which is a continuation-in-part of application Ser. No. 595,156, filed Mar. 30, 1984, abandoned.

BACKGROUND OF THE DISCLOSURE

1. Field of the Invention

The instant invention is directed to a class of substituted oxime carbamate compounds. More specifically, the instant invention is directed to a class of substituted oxime carbamates of tetrahydrothienyl alkanones useful as pesticides.

2. Background of the Prior Art

Harmful pests, especially insects, nematodes and acarids, attack a wide variety of ornamental and agricultural plants. These pests inflict damage by consuming foliage, withdrawing vital juices from the plants, secreting toxins and transmitting diseases. There is thus a continuing need to develop new means to control these pests in the interests of maintaining the plants they attack.

Tetrahydrothiophenes are well known in the art. Similarly oxime carbamates are known to the art. Certain compounds of each of these compound categories are known to be useful in pesticidal applications. These compounds, however, do not provide the pesticidally effective properties of compounds which incorporate both functional groups in their structure.

SUMMARY OF THE INVENTION

The instant invention is directed to a new class of compounds which incorporate both the properties of tetrahydrothienyl alkanones as well as substituted oxime carbamates. These compounds exhibit excellent pesticidal control of a wide variety of insects, nematodes and acarids.

In accordance with the instant invention, a new class of compounds or salts thereof having the formula

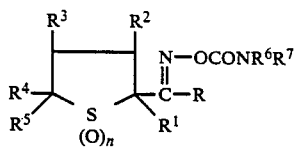

wherein R is $C_1$–$C_4$ alkyl, cyclopropyl, $C_2$–$C_4$ alkoxyalkyl, $C_2$–$C_4$ alkylthioalkyl, $C_4$–$C_8$ dialkylaminoalkyl, $C_2$–$C_4$ alkylsulfinylalkyl, $C_2$–$C_4$ alkylsulfonylalkyl, phenyl, $C_7$–$C_9$ aralkyl, $C_7$–$C_9$ alkaryl, furyl, thienyl or pyridyl; $R^1$ is hydrogen, halo or $C_1$–$C_4$ alkyl; $R^2$, $R^3$, $R^4$ and $R^5$ are the same or different and are hydrogen or $C_1$–$C_4$ alkyl; $R^6$ and $R^7$ are the same or different and are hydrogen, $C_1$–$C_4$ alkyl, allyl, benzyl or tolyl with the proviso that $R^6$ and $R^7$ are not simultaneously hydrogen; and n is 0, 1 or 2. These compounds thereof are useful as pesticides, effective in the control of insects, nematodes and acarids.

Another aspect of the instant invention is directed to intermediates useful in the formation of the pesticidally effective compounds of this invention. The first of these intermediates has the structural formula

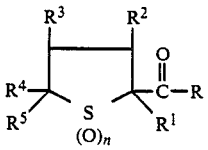

where R, $R^1$, $R^2$, $R^3$, $R^4$, $R^5$ and n have the meanings given above for the pesticidally effective compound.

The second intermediate, a ketoxime, has the formula

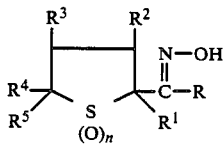

where R, $R^1$, $R^2$, $R^3$, $R^4$, $R^5$ and n have the meanings given above for the pesticidally effective compound.

Yet a third intermediate useful in the synthesis of the pesticidally effective compound of this invention has the structural formula $$Q\text{—}CHR^2CHR^3CR^4R^5SCH(COR)_2$$

where R, $R^2$, $R^3$, $R^4$ and $R^5$ have the meanings given above and Q is a leaving group.

The instant invention is furthermore directed to a composition comprising the pesticidally effective compound and a carrier therefor. These compositions are effective pesticides.

In still another aspect of this invention, a method for controlling pests, especially insects, nematodes and acarids, comprising applying a pesticidally effective amount of a compound having the formula

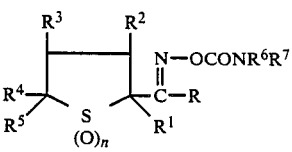

where R, $R^1$, $R^2$, $R^3$, $R^4$, $R^5$, $R^6$, $R^7$ and n have the meanings given above is disclosed.

In yet another aspect of the instant invention, a method for making the first recited intermediate compound is provided. In this method, a tetrahydrothiophene 1,1-dioxide is reacted with a strong base at a temperature in the range of between −70° and 0° C. to produce an intermediate carbanion which may be reacted with an ester to yield the ketone intermediate of this invention upon acidification of the reaction mixture. Alternatively, the carbanion may be reacted with a nitrile to give an imine intermediate which is then hydrolyzed with an acid to the ketone intermediate of this invention. The intermediate ketone of this invention may also be produced by cyclization of $Q\text{—}CHR^2CHR^3CR^4R^5SCH(COR)_2$, where Q, R, $R^2$, $R^3$, $R^4$ and $R^5$ have the meanings given above, in the presence of an alkali alkoxide.

Another aspect of the instant invention resides in a process for forming the second mentioned intermediate of the instant invention. In this process the first intermediate is reacted with a hydroxylamine salt in the presence of a base in an appropriate solvent.

Still another aspect of the present invention resides in a process for forming the compound Q—CHR$^2$CHR$^3$CR$^4$R$^5$SCH(COR)$_2$ where Q, R$^2$, R$^3$, R$^4$ and R$^5$ have the meanings given above. In this process a compound of the formula XCH(COR)$_2$ is reacted with a compound of the formula HO—CHR$^2$CHR$^3$CR$^4$R$^5$SH to form HOCHR$^2$CHR$^3$CR$^4$R$^5$SCH(COR)$_2$ which is then halogenated or esterified to produce the intermediate compound Q—CHR$^2$CR$^3$CR$^4$R$^5$SCH(COR)$_2$ where Q, R, R$^2$, R$^3$, R$^4$ and R$^5$ have the meanings given above; and X is halo.

Yet another aspect of this invention is a process for making the pesticidally effective compound of the present invention. In this process the second recited aintermediate is reacted with an isocyanate compound having the formula R$^6$—N=C=O. Alternately, the second intermediate is reacted with a carbamyl halide having the formula R$^6$R$^7$NC(O)X in the presence of a hydrogen chloride acceptor. Yet still another method of forming the pesticidally effective compound of this invention entails the reaction of the ketoxime intermediate with phosgene. The product of that reaction is reacted with a primary or secondary amine to produce the desired compound.

DETAILED DESCRIPTION

The compound of the instant invention has the structural formula

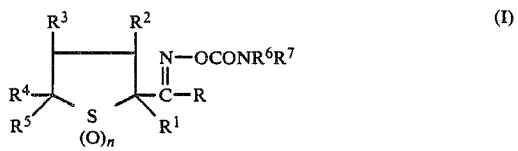

(I)

where R is C$_1$–C$_4$ alkyl, cyclopropyl, C$_2$–C$_4$ alkoxyalkyl, C$_2$–C$_4$ alkylthioalkyl, C$_4$–C$_8$ dialkylaminoalkyl C$_2$–C$_4$ alkylsulfinylalkyl, C$_2$–C$_4$ alkylsulfonylakyl, phenyl, C$_7$–C$_9$ aralkyl, C$_7$–C$_9$ alkaryl, furyl, thienyl or pyridyl; R$^1$ is hydrogen, halo or C$_1$–C$_4$ alkyk; R$^2$, R$^3$, R$^4$ and R$^5$ are the same or different and are hydrogen or C$_1$–C$_4$ alkyl; R$^6$ and R$^7$ are the same or different and are hydrogen, C$_1$–C$_4$ alkyl, allyl, benzyl or tolyl with the proviso that R$^6$ and R$^7$ are not simultaneously hydrogen; and n is 0, 1 or 2.

More preferably, the instant invention is directed to a compound having the formula (I) where R is C$_1$–C$_3$ alkyl, cyclopropyl, C$_2$–C$_3$ alkoxyalkyl, C$_3$–C$_4$ alkylthioalkyl, C$_3$–C$_4$ alkylsulfinylalkyl, C$_3$–C$_4$ alkylsulfonylalkyl, furyl, thienyl or pyridyl; and R$^6$ and R$^7$ are different and are hydrogen and methyl.

Most preferably, the instant invention is directed to a compound having the formula (I) where R is C$_1$–C$_2$ alkyl, cyclopropyl, methylthiomethyl, methylsulfonylmethyl, furyl, thienyl or pyridyl.

The instant invention is also directed to an intermediate compound having the formula

QCHR$^2$CHR$^3$CR$^4$R$^5$SCH(COR)$_2$ (II)

where R, R$^2$, R$^3$, R$^4$ and R$^5$ have the meanings given in the broadest definition of compound I and Q is a leaving group. More preferably, R has the meanings given above for the more preferable case of compound I; and Q is an alkylsulfonyloxy, arylsulfonyloxy or halo. Most preferably, R has the meanings given above for the most preferable definition of Compound I; and Q is methylsulfonyloxy or p-toluenesulfonyloxy. In a particularly preferred embodiment, Compound II is 3-[3-(Methylsulfonyloxy)propylthio]-2,4-pentanedione. Compound II is useful as an intermediate in the synthesis of Compound I.

A further aspect of the present invention is a compound having the structural formula

(III)

where R, R$^1$, R$^2$, R$^3$, R$^4$, R$^5$ and n have the broadest meanings given above for the compound having the formula (I). More preferably, Compound (III) has the meanings of R recited for the preferable embodiment of Compound I. Most preferably, R has the meaning of the most preferred embodiment of Compound (I).

Compound III is precursor useful in the making of the pesticidally effective compound having the formula (I).

Another aspect of the present invention is a compound having the formula

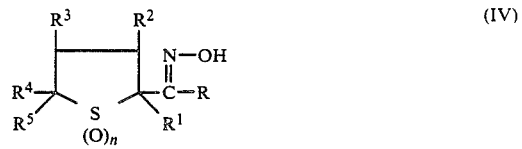

(IV)

wherein R, R$^1$, R$^2$, R$^3$, R$^4$, R$^5$ and n have the meanings given for Compound (I). Preferred and most preferred embodiments of this compound have the meanings of R given above for the preferred and most preferred embodiments of compound I.

A process is provided for the synthesis of intermediate Compound II. In this process a compound having the formula

XCH(COR)$_2$ (V)

where R has the meanings given in the broadest meanings for Compound I; and X is a halo is reacted with a compound having the formula

HOCHR$^2$CHR$^3$CR$^4$R$^5$SH (VI)

The reaction is preferably run at a temperature in the range of 10° to 50° C., preferably ambient, in the presence of an organic base, which acts as a hydrogen halide acceptor. The preferred base is pyridine. A product of this reaction is

HOCHR$^2$CHR$^3$CR$^4$R$^5$SCH(COR)$_2$ (VII)

wherein R, R$^2$, R$^3$, R$^4$ and R$^5$ have the same meanings as given above. Compound VII is reacted with a halogenating or esterifying agent to produce the compound of this invention, Compound II.

This latter reaction occurs at low temperature, from −20° C. to 0° C., in a solvent in the presence of a base.

In preferred embodiments the solvent may be methylene chloride, pyridine, toluene or tetrahydrofuran. The preferred base is triethylamine or pyridine.

In an aspect of the instant invention, a process is provided for making the ketone precursor (Compound III). In this process, a tetrahydrothiophene 1,1-dioxide is reacted with a strong base. The dioxide, preferably tetrahydrothiophene 1,1-dioxide, is reacted in solution, employing an aprotic solvent, preferably tetrahydrofuran. The strong base with which the dioxide is reacted is preferably n-butyl lithium or lithium diisopropylamide. This reaction occurs at a temperature in the range of between $-70°$ and $0°$ C. The product of this reaction is an alpha-sulfonyl carbanion. In one preferred embodiment, the carbanion is reacted with an ester, preferably a $C_1$-$C_4$ alkyl ester, to give the compound having the formula (III) upon acidification of the reaction mixture.

In another preferred embodiment compound III is formed by another process. Initially the carbanion is formed as in the preceding method. However, the carbanion is then reacted with a nitrile to give an imine intermediate. The imine, in turn, is hydrolyzed with an acid to produce Compound III.

In yet another method of obtaining compound III, the ketone intermediate of this invention, compound II, preferably 3-[3-(methylsulfonyloxy)propylthio]-2,4-pentanedione, is cyclized in the presence of an alkali alkoxide, preferably sodium alkoxide, dissolved in a lower alkanol to produce compound III. In this method compound III is limited to the case where n is 0.

In order to produce the embodiment wherein compound III is characterized by $R^1$ being $C_1$-$C_4$ alkyl or halo, compound III, where n is 2 and $R^1$ is hydrogen, is alkylated or halogenated at the alpha position substituted by the acyl group. In this reaction an alkali hydride, preferably sodium hydride, is reacted with compound III, where n is 2 and $R^1$ is hydrogen, in an aprotic solvent, preferably tetrahydrofuran, at a temperature in the range of $-10°$ to $25°$ C., to produce a carbanion. The carbanion is reacted with a $C_1$-$C_4$ alkyl attached to a leaving group or halogen. Leaving groups, well known in the art, preferred for use in this reaction include halides, sulfates, tosylates and the like.

An aspect of the instant invention includes the formation of the compound IV. These compounds, ketoxime intermediates, are prepared from the ketone compound, Compound III, by reaction of Compound II with hydroxylamine salt, preferably hydroxy amine hydrochloride in the presence of a base. Preferred bases within the contemplation of this invention include sodium acetate, sodium hydroxide and pyridine. The reaction also occurs in the presence of a solvent, preferably, a lower alkanol, water or mixtures thereof. In this reaction the ketoxime product is usually obtained as a mixture of the syn- and anti-isomers.

In still another aspect of the present invention processes are provided for synthesizing Compound I. Compounds having the structural formula (I) are prepared, in one preferred embodiment, by reacting a ketoxime compound (Compound III) with an isocyanate having the formula $R^6$—N=C=O in an aprotic solvent. The isocyanate having the formula $R^6$—N=C=O is one in which $R^6$ has the meanings given earlier for that radical. Among the preferred aprotic solvents useful in this reaction are toluene, tetrahydrofuran and dimethylformamide. This reaction is carried out at a temperature of between $0°$ C. and the boiling point of the aprotic solvent. Preferably, the temperature of reaction is between $20°$ and $70°$ C. Optionally, a catalyst may be provided in this reaction. Preferred catalysts for this use include triethylamine and dibutyltin diacetate. The catalyst, of course, reduce the time of reaction. It is emphasized, however, that the use of a catalyst is not essential to the commercial exploitation of this reaction.

In another preferred embodiment, compound I is formed by the reaction of the ketoxime compound, having the formula (IV), with a carbamyl halide having the formula $R^6R^7NC(O)X$ where X is halo and $R^6$ and $R^7$ have the meanings given above. This reaction occurs in the presence of a hydrogen halide acceptor. Among the hydrogen halide acceptors preferred for use in this reaction is triethylamine in a suitable aprotic solvent. A particularly preferred aprotic solvent is tetrahydrofuran.

The temperature of the reaction between Compound IV and the carbamyl halide of this invention is in the range of between $20°$ and $150°$ C. Again, it is optional to employ a catalyst which shortens the reaction time. If a catalyst is employed in this reaction, 4-dimethylaminopyridine is particularly preferred.

In another method of forming compound I the ketoxime intermediate, compound IV, is reacted with phosgene. This reaction occurs at a temperature of $-10°$ to $25°$ C. in the presence of a hydrogen halide acceptor, for example, triethylamine, and usually in the presence of an aprotic solvent. The product of this reaction is, in turn, reacted with a primary or secondary amine having the formula $R^6R^7NH$ where $R^6$ and $R^7$ have the meanings given above. This latter reaction occurs at the same conditions as the phosgenation reaction.

Yet a fourth method for producing compound I of this invention involves the formation of compound I, where n is 1 or 2, from starting compound I, where n is 0. In this method the oxime carbamate is oxidized. In this oxidation reaction a peroxy acid reacts with compound I (n=0) in a suitable solvent. M-chloroperoxybenzoic acid is particularly preferred in this application. Methylene chloride is preferred for use as the solvent. This reaction occurs at a temperature in the range of between $-20°$ and $10°$ C. The degree of oxidation (cyclic sulfoxide or cyclic sulfone) is a function of the molar equivalents of oxidizing agent employed in the reaction. If one molar equivalent of the peroxy acid is reacted, a cyclic sulfoxide (n=1) results. If two or more equivalents of the oxidizing agent are reacted, a sulfone (n=2) is formed.

Other oxidizing agents besides peroxy acids may be employed. Among the preferred alternative oxidating agents useful in this method are hydrogen peroxide, sodium meta-periodate and potassium permanganate.

It should be appreciated that compound I wherein R is alkylthioalkyl, may be converted to the corresponding alkylsulfinylalkyl or alkylsulfonylalkyl by the method discussed above.

The compounds having the formula (I) are useful as pesticides, specifically insecticides, nematocides and acaricides. To be effective in this application, Compound I may be applied neat, that is, alone, as a liquid composition, or as a two phase composition.

In an embodiment wherein a pesticidally effective liquid composition is employed, the composition comprises Compound I with a liquid inert carrier. The carrier may be a suitable solvent or liquid suspending agent. Among the carriers commonly employed in these appications are water, alcohol, ketones, phenol, toluene or xylene. Optionally, the composition may also include one or more surface-active agents and/or inert diluents which may be added to the composition to facilitate handling. Another liquid composition within the contemplation of this invention is an emulsion which, of course, includes the incorporation into the composition of an emulsifying agent.

In a preferred embodiment wherein a two phase composition is provided, the Compound I is admixed with, or absorbed on, a solid inert carrier. Among the inert carriers within the contemplation of this invention are mineral silicates, such as mica, talc, prophyllite and clays. These solid particles are powders. The active agent is absorbed on these particles which are then suspended in a suitable suspending agent, preferably, water. In this composition, a surface-active dispersing agent is provided. The surface-active dispersing agent may be anionic, non-ionic or cationic. Such surface-active agents are well known in the art. Reference is made to U.S. Pat. No. 2,547,734, columns 3 and 4, which provide detailed examples of such surface-active agents within the contemplation of this invention. It is oftentimes preferred that such suspensions be provided as concentrates and that subsequent diluting agents, especially water, be added to provide aqueous suspensions of Compound I at the desired concentration for usage.

Another embodiment of the composition of this invention employs a granular or pelletized form of carrier, rather than the powdered carrier discussed above. Granular or pelletized carriers, within the contemplation of this invention, include granular clays, vermiculite, charcoal and corn cobs. The formation of a composition which employs this granular type of formulation is the same as discussed above for a powdered formulation. Granular formulations are preferably applied by broadcasting, side dressing, soil incorporation or seed treatment, methods known to those skilled in the pesticidal arts. The granules may be suspended in water or applied directly.

Other methods for applying the pesticidal compound or composition of this invention include aerosol application of the effective pesticidal compound or composition to loci to be protected. In one preferred embodiment of the aerosol method of application, solutions are formed. In this embodiment compound I is dissolved in an inert aerosol solvent which is a gas at ambient conditions, but is stored as a liquid solution under pressure. Alternatively, the active agent is first dissolved in a less volatile solvent to form a solution. The solution is then admixed with a highly volatile liquid aerosol carrier. The aerosol carrier may be inert or active itself. Thus, the aerosol carrier may be a pesticide, active against insects, acarids, fungi, bacteria, or the like.

The pesticidal formulations of this invention incorporate concentrations of Compound I effective for the particular method of control. These amounts can vary widely. Typically, the concentration range is from 0.1 to 95% of the active ingredient. Spray dilutions which contain from a few parts per million to full strength concentrates, applied by ultra low volume techniques, are within the contemplation of this invention. Concentrations per unit area can vary from 0.01 to 50 pounds per acre, preferably from 0.1 to 10 pounds per acre.

To control the pests against which Compound I is effective, the compound may be applied directly to the pests to be controlled, to the plants upon which they feed, or both. Another method for controlling the pests, within the contemplation of this invention, involves application of Compound I to the soil or other medium in which these pests live.

The following examples are given to illustrate the invention embodied in this application. Therefore, the scope of the invention should not be limited to these examples.

EXAMPLE 1

Formation of 1-(tetrahydro-1,1-dioxo-2-thienyl)ethanone Compound I)

120 g (1.0 mol) of tetrahydrothiophene 1,1-dioxide was introduced into a nitrogen-flushed, 5 liter, 3-neck flask fitted with a mechanical stirrer, thermometer, additional funnel and gas inlet bubbler. Also, introduced into the flask were 2 liters of dry tetrahydrofuran (THF). Both ingredients were introduced under an atmosphere of nitrogen. The resultant solution was cooled to $-70°$ C. by employing an acetone-dry ice bath. To this solution was added 627 ml (1 mol) of a solution of 1.6M n-butyl lithium in hexane. This addition occurred with stirring over a period of 1.75 hours. During this addition, the temperature was maintained at $-70°$ C. The reaction mixture was stirred for an additional 1.5 hours, still maintaining a temperature of $-70°$ C. At this point, 98 ml (1 mol) of ethyl acetate was added rapidly with vigorous stirring. After one-half hour, the resultant reaction slurry was made acidic with the addition of 10% hydrochloric acid. Sodium chloride was then added and the organic phase was separated and dried over magnesium sulfate. Removal of the solvent in a rotary evaporator left 150 g of an oil which was then dissolved in 400 ml of benzene. The benzene solution was extracted with 600 ml of 10% sodium hydroxide. The aqueous phase was separated, acidified with cold concentrated hydrochloric acid, taken up in chloroform and dried over magnesium sulfate. Removal of the chloroform afforded 126 ml of a yellow oil. Analysis by gas chromatography showed the mixture to contain tetrahydrothiophene 1,1-dioxide (starting compound) and 1-(tetrahydro-1,1-dioxo-2-thienyl)ethanone in a ratio of 1:4. Distillation of the crude product, using a Nester Faust [trademark] spinning band column under reduced pressure, provided 68 g of 1-(tetrahydro-1,1-dioxo-2-thienyl)ethanone, b.p. 88°–90° C. at 0.1 mm Hg (13 Pa).

EXAMPLE 2

Preparation of (tetrahydro-1,1-dioxo-2-thienyl)phenylmethanone (Compound 2)

48 g (0.4 Mol) of tetrahydrothiophene 1,1-dioxide and 600 ml of THF were cooled to $-70°$ C. and introduced into the 5 liter flask described in Example 1. To this was added 142 ml (0.37 mol) of 2.6M n-butyl lithium in hexane, which was added, with vigorous stirring under nitrogen, over a period of 40 minutes. The reaction mixture was stirred for 10 minutes and 38.5 g (0.37 mol) of benzonitrile was added to this mixture over a period of one-half hour. The reaction mixture was allowed to warm to room temperature and was stored overnight with stirring. The following morning the thick reaction mixture was poured into an ice-water mixture. The organic phase was combined with a diethyl ether extract of the aqueous phase and dried over magnesium sulfate. Removal of the solvent afforded 79.2 g of a viscous oil. The viscous oil was combined with 300 ml of 6N hydrochloric acid and heated under reflux for one hour. After cooling to room temperature, the aqueous phase was decanted from a thick brown oil which was triturated with diethyl ether. The resultant solid was recrystallized from 95% ethanol to give 60 g of (tetrahydro-1,1-dioxo-2-thienyl)phenylmethanone, m.p. 90°–94° C.

EXAMPLE 3

Preparation of 1,1-(dimethylethyl))tetrahydro-1,1-dioxo-2-thienyl)methanone (Compound 3)

To a dried, nitrogen-filled 1 liter, 3-neck flask, fitted with a mechanical stirrer, additional funnel, thermometer and nitrogen inlet bubbler containing a solution of 42 ml (0.3 mol) of diisopropyl amine and 300 ml of THF, was added 193 ml (0.3 mol) of 1.5M n-butyl lithium in n-hexane over a period of one-half hour while cooling the flask with an ice-water bath. 72 g (0.6 Mol) of tetrahydrothiophene 1,1-dioxide was added in 20 minutes to form a white slurry. The reaction mixture was warmed to 30° C. and maintained at this temperature for 1 hour. 34 ml (0.3 Mol) of trimethylacetonitrile was added to the reaction mixture over a period of 10 minutes. The reaction mixture was heated to reflux for 6 hours and stirred overnight at room temperature. Hydrolysis of this reaction mixture occurred by the addition of a saturated aqueous solution of ammonium chloride. The organic phase resulting therefrom was separated, washed with aqueous sodium chloride and dried over magnesium sulfate. The product, a yellow liquid, weighed 76 g. Its infrared spectrum exhibited a sharp absorption at 1635 cm$^{-1}$ for N=C. The product was added to 500 ml of 6N hydrochloric acid. After an initial exotherm, the mixture was heated to reflux for 2 hours. After cooling to room temperature, the bottom organic phase was separated, combined with one diethyl ether extract of the aqueous portion and dried over magnesium sulfate. Removal of the ether left 40 g of an oil. A chloroform extract of the aqueous phase gave an additional 22 g of an oil. The combined crude product was distilled, using a vacuum jacketed apparatus under reduced pressure, to give 42 g of (1,1-dimethylethyl)(tetrahydro-1,1-dioxo-2-thienyl)methanone, b.p. 95°–97° C. (0.1 mm Hg), m.p. 53°–56° C. Upon recrystallization from cyclohexane/ethyl acetate, a small sample of the above-recited product was obtained having a melting point of 56.5°–57° C.

EXAMPLE 4

Preparation of 1-(tetrahydro-2-methyl-1,1-dioxo-2-thienyl)ethanone (Compound 4)

A solution of 12.0 g (74 mmol) of 1-(tetrahydro-1,1-dioxo-2-thienyl)ethanone in 25 ml of THF was added dropwise over a period of 1 hour to a stirred slurry of 3.0 g (75 mmol) of a 60% dispersion of sodium hydride in mineral oil (the oil was removed by two washers with hexane) and 25 ml of THF under an atmosphere of nitrogen. The addition occurred while the flask was cooled in an ice-water bath. Salt, which formed at the end of the dropwise addition, required the addition of 20 ml of THF to facilitate stirring. The reaction mixture was allowed to warm to room temperature. At this time, 11.4 g (80 mmol) of iodomethane was added. This addition took 5 minutes. The reaction was stirred at room temperature for 30 minutes and heated to 55° C. for 17 hours. The cool reaction mixture was separated into aqueous and organic phases. The organic layer was separated, dried over magnesium sulfate and stripped of solvent to yield 7.8 g of an orange colored oil. The crude product was distilled. The distilled product had a boiling point of 90°–95° C. (0.1 mm Hg). The distillate crystallized on standing and was recrystallized from ethyl acetate-hexane to give 5.9 g of 1-(tetrahydro-2-methyl-1,1-dioxo-2-thienyl)ethanone, m.p. 47°–48° C.

EXAMPLE 5

Preparation of 1-(tetrahydro-2-thienyl)ethanone (Compound 5)

To a stirred solution of 8.1 g (34 mmol) of 3-[3-(methylsulfonyloxy)propylthio]-2,4-pentanedione and 35 ml of methanol, disposed in a 1 liter, 3-neck flask, was added 8.0 ml of 25% solution of sodium methoxide in methanol over a period of 1 hour. The addition occurred at room temperature. The reaction mixture was left undisturbed, but for stirring, for 18 hours. The mixture was then heated to 50° C. for 1 hour. After cooling the heated mixture to room temperature, the reaction mixture was poured into aqueous ammonium chloride and extracted with 50 ml of methylene chloride. The extract was dried over magnesium sulfate and stripped of solvent to yield 5 g of a dark liquid. Distillation of this crude product resulted in 2.9 g of 1-(tetrahydro-2-thienyl)ethanone, b.p. 112°–120° C. at 43 mm Hg (5.59 kPa).

EXAMPLE 6

Preparation of Compounds 6–16

Additional ketone intermediate compounds were prepared in accordance with the procedures of either Examples 1 or 2. These compounds, as well as Compounds 1–5, made in accordance with the procedures of Examples 1–5, respectively, are summarized in Table 1 below:

TABLE 1

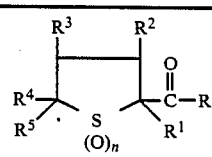

| Comp. No. | n | R | R$^1$ | R$^2$ | R$^3$ | R$^4$ | R$^5$ | m.p. or b.p. (mm Hg) °C. | Method of Example |
|---|---|---|---|---|---|---|---|---|---|
| 1 | 2 | CH$_3$ | H | H | H | H | H | 88–90 (0.1) | 1 |
| 2 | 2 | C$_6$H$_5$ | H | H | " | " | " | 90–94 | 2 |
| 3 | 2 | C(CH$_3$)$_3$ | H | H | " | " | " | 53–56° | 3 |

TABLE 1-continued

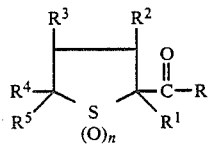

| Comp. No. | n | R | $R^1$ | $R^2$ | $R^3$ | $R^4$ | $R^5$ | m.p. or b.p. (mm Hg) °C. | Method of Example |
|---|---|---|---|---|---|---|---|---|---|
| 4 | 2 | $CH_3$ | $CH_3$ | H | " | " | " | 47–48° | 4 |
| 5 | 0 | $CH_3$ | H | H | " | " | " | 112–120 (43) | 5 |
| 6 | 2 | $CH_2CH_3$ | H | H | " | " | " | 87–103 (0.08) | 1 |
| 7 | 2 | c-$C_3H_5$ | H | H | " | " | " | 90–91 | 1 |
| 8 | 2 | —$(CH_2)_3CH_3$ | H | H | " | " | " | 113–123 (0.1) | 1 |
| 9 | 2 | $CH_2C_6H_5$ | H | H | " | " | " | 107–109 | 1 |
| 10 | 2 | $(CH_2)_2SCH_3$ | H | H | " | " | " | oil | 1 |
| 11 | 2 | $CH(CH_3)_2$ | H | H | " | " | " | 53–55 | 1 |
| 12 | 2 | 3-$CH_3C_6H_4$ | H | H | " | " | " | 80–82 | 2 |
| 13 | 2 | 2-furyl | H | H | " | " | " | 93–96 | 1 |
| 14 | 2 | 2-thienyl | H | H | " | " | " | 110–115 | 1 |
| 15 | 2 | 3-pyridyl | H | H | " | " | " | oil | 1 |
| 16 | 2 | $CH_2SCH_3$ | H | H | " | " | " | 58–59 | 1 |

EXAMPLE 7

Preparation of 1-(tetrahydro-1,1-dioxo-2-thienyl)ethanone, oxime (Compound 17)

A mixture of 12.4 g (0.07 mol) of 1-(tetrahydro-1,1-dioxo-2-thienyl)ethanone, 14 g (0.2 mol) of hydroxylamine hydrochloride, 14 g (0.17 mol) of sodium acetate and 75 ml of water was heated in a steam bath for 4.5 hours. Upon cooling, the reaction mixture was extracted five times with 100 ml portions of chloroform. The combined extracts were dried over magnesium sulfate and the solvent was removed from the filtrate on a rotary evaporator. The resultant oil, upon standing for a period of time, resulted in the crystallization of large crystals. The crystal product was recrystallized from benzene giving 7.6 g of 1-(tetrahydro-1,1-dioxo-2-thienyl)ethanone, oxime, m.p. 79°–80° C.

EXAMPLE 8

Preparation of 1-(tetrahydro-1,1-dioxo-2-thienyl)ethanone, oxime (Compound 17)

In an alternate method of synthesizing Compound 17, 28.7 g (0.4 mol) of hydroxylamine hydrochloride was added to a solution of 16 g (0.4 mol) of sodium hydroxide and 100 ml of water. Seventy-four grams of a mixture containing 1-(tetrahydro-1,1-dioxo-2-thienyl)ethanone (0.33 mol) and tetrahydrothiophene 1,1-dioxide was added to the solution contained in a 1 liter flask. After an exotherm, the reaction mixture was stirred at room temperature overnight. The reaction mixture was extracted twice with chloroform and the combined extract dried over magnesium sulfate. Removal of the solvent afforded 74 g of viscous oil. Tetrahydrothiophene 1,1-dioxide, present in the starting ketone, was removed by short-path distillation at 0.05 mm Hg (6.5 Pa). The distillation residual oil was triturated with toluene to give 48.2 g of a white solid, melting range 66°–75° C. The infrared spectrum (KBr disk) of the product was identical to that of 1-(tetrahydro-1,1-dioxo-2-thienyl)ethanone, oxime prepared in accordance with the procedure of Example 7.

EXAMPLE 9

Preparation of 1-(tetrahydro-1,1-dioxo-2-thienyl)ethanone, oxime (Compound 17)

In yet another method for forming Compound 17, 282.6 of a mixture containing 1-(tetrahydro-1,1-dioxo-2-thienyl)ethanone (1.3 mol) was added to a flask containing a mixture of 107.5 g (1.5 mol) of hydroxylamine hydrochloride, 118.6 g (1.5 mol) pyridine and 500 ml of isopropanol. The addition occurred with stirring at room temperature. A short time after the introduction was completed, and while stirring continued, the temperature rose to 40° C. and the mixture became homogeneous. The reaction mixture was heated to reflux for 6 hours and then allowed to remain undisturbed, but for stirring, at room temperature. Isopropanol was removed on a rotary evaporator giving a residue which was partitioned between chloroform (1 liter) and an aqueous solution of sodium chloride. The chloroform portion was washed once with 300 ml of a saturated solution of sodium chloride and dried over magnesium sulfate. Removal of the chloroform on the rotary evaporator afforded 252 g of an oil. Tetrahydrothiophene 1,1-dioxide, present in the starting ketone, was distilled from the product at 0.04 mm Hg (5.2 Pa). The remaining residual oil was triturated with 500 ml of toluene yielding 193 g of 1-tetrahydro-1,1-dioxo-2-thienyl)ethanone, oxime, melting range 70°–80° C. The infrared spectrum of the product was consistent with the spectrum for the oxime made in accordance with Examples 7 and 8.

EXAMPLE 10

Preparation of Compounds 18–32

Additional compounds, Compounds 18–32, were made in accordance with the procedures of Examples 7, 8 and 9. These compounds, as well as compound 17, are summarized in Table II below:

TABLE 2

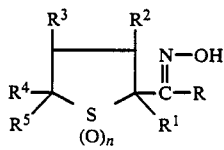

| Comp. No. | n | R | $R^1$ | $R^2$ | $R^3$ | $R^4$ | $R^5$ | m.p. or b.p. (mm Hg) °C. | Method of Example |
|---|---|---|---|---|---|---|---|---|---|
| 17 | 2 | $CH_3$ | H | H | H | H | H | 79–80 | 7 |
| 17 | 2 | $CH_3$ | H | H | " | " | " | 66–75 | 8 |
| 17 | 2 | $CH_3$ | H | H | " | " | " | 70–80 | 9 |
| 18 | 2 | $C_6H_5$ | H | H | " | " | " | 113–121 | 9 |
| 19 | 2 | $C(CH_3)_3$ | H | H | " | " | " | 182–185(dec)* | 9 |
| 20 | 2 | $CH_3$ | $CH_3$ | H | " | " | " | 121–124 | 9 |
| 21 | 0 | $CH_3$ | H | H | " | " | " | oil | 8 |
| 22 | 2 | $CH_2CH_3$ | H | H | " | " | " | 99–112 | 9 |
| 23 | 2 | $c\text{-}C_3H_5$ | H | H | " | " | " | 113–146 | 9 |
| 24 | 2 | $(CH_2)_3CH_3$ | H | H | " | " | " | 71–76 | 9 |
| 25 | 2 | $CH_2C_6H_5$ | H | H | " | " | " | 134–137 | 9 |
| 26 | 2 | $(CH_2)_2SCH_3$ | H | H | " | " | " | oil | 9 |
| 27 | 2 | $CH(CH_3)_2$ | H | H | " | " | " | 106–114 | 9 |
| 28 | 2 | $3\text{-}CH_3C_6H_4$ | H | H | " | " | " | 72–120 | 9 |
| 29 | 2 | 2-furyl | H | H | " | " | " | 119–129 | 9 |
| 30 | 2 | 2-thienyl | H | H | " | " | " | 154–161 | 9 |
| 31 | 2 | 3-pyridyl | H | H | " | " | " | 227(dec) | 8 |
| 32 | 2 | $CH_2SCH_3$ | H | H | " | " | " | 72–75 | 8 |

*Temperature of decomposition

EXAMPLE 11

Preparation of 1-(tetrahydro-1,1-dioxo-2-thienyl)ethanone,O-[(methylamino)carbonyl]oxime (Compound 33)

A mixture of 4.0 g (22.6 mmol) of 1-(tetrahydro-1,1-dioxo-2-thienyl)ethanone, oxime, 50 ml of toluene and 1.3 ml (22.6 mmol of methylisocyanate was stirred at room temperature for 6 days. After heating the reaction mixture to reflux for 2 hours, the mixture was cooled and the resultant solid filtered. The filtrate comprised 5.1 g of a white powder. Recrystallization from ethyl acetate yielded 4.2 g of 1-(tetrahydro-1,1-dioxo-2-thienyl)ethanone, O-[(methylamino)-carbonyl]oxime, m.p. 119°–120° C.

EXAMPLE 12

Preparation of (tetrahydro-1,1-dioxo-2-thienyl)-3-pyridylmethanone,O-[(methylamino)carbonyl]oxime (Compound 34)

A mixture of 4.8 g (20 mmol) of (tetrahydro-1,1-dioxo-2-thienyl)-3-pyridylmethanone, oxime, 25 ml of dimethylformamide and 1.2 g (21 mmol) of methyl isocyanate, contained in a Wheaton [trademark] pressure bottle, was heated to 70° C. with stirring, for 5 hours. After cooling to room temperature, the reaction solution was poured into 175 ml of water. The product was extracted from the aqueous solution with 2 portions of chloroform (150 ml). The extracts were combined and dried over magnesium sulfate. Removal of the solvent under reduced pressure gave 5.3 g of a viscous oil which crystallized on standing. The solid was recrystallized from isopropanol to give 3.5 g of an off-white solid which was (tetrahydro-1,1-dioxo-2-thienyl)-3-pyridylmethanone,O-[(methylamino)carbonyl], oxime, melting range 154°–165° C.

EXAMPLE 13

Preparation of (tetrahydro-1,1-dioxo-2-thienyl)-3-pyridylmethanone, O-[(methylamino)carbonyl]oxime, hydrochloride (Compound 35)

Hydrogen chloride gas was bubbled into a slightly cloudy solution of 300 ml of chloroform and 3.4 g (11.4 mml) of (tetrahydro-1,1-dioxo-2-thienyl)-3-pyridylmethanone, O-[(methylamino)carbonyl]oxime for 10 minutes. The chloroform and excess hydrogen chloride were removed under reduced pressure to give 3.8 g of a light, foamy solid which was (tetrahydro-1,1-dioxo-2-thienyl)-3-pyridylmethanone, O-[(methylamino)carbonyl]oxime, hydrochloride. The product was a tacky solid without an observable melting point.

EXAMPLE 14

Preparation of 1-(tetrahydro-1,1-dioxo-2-thienyl)ethanone, O-[(dimethylamino)carbonyl]oxime (Compound 36)

A mixture of 3.0 g (17 mmol) of 1-(tetrahydro-1,1-dioxo-2-thienyl)ethanone, oxime, 25 ml THF, 1.8 g (17 mmol) of dimethylcarbamyl chloride, 1.7 g (17 mmol) of triethylamine and 0.1 g of 4-(dimethylamino)pyridine was heated to reflux for 3 hours. The reaction mixture was poured into cold water. The product of this reaction was extracted with 75 ml of chloroform. The product was dried over magnesium sulfate and the extract stripped of solvent leaving an amber oil which crystallized on standing overnight. Recrystallization of the product from toluene afforded 2.7 g of an off-white solid, 1-(tetrahydro-1,1-dioxo-2-thienyl)ethanone, O-[(dimethylamino)carbonyl]oxime, m.p. 114°–116° C.

EXAMPLE 15

Preparation of 1-(tetrahydro-1,1-dioxo-2-thienyl)-2-(methylsulfonyl)ethanone, O-[(methylamino)carbonyl]oxime (Compound 37)

To a stirred slurry of 5.4 g (25 mmol) of m-chloroperoxybenzoic acid (80–85%) and 50 ml of methylene chloride in a flask, which was disposed in an ice-water bath, was slowly added a solution of 3.3 g (12 mmol) of 1-(tetrahydro-1,1-dioxo-2-thienyl)-2-(methylsulfonyl)ethanone, O-[(methylamino)carbonyl]oxime, m.p. 164–167.

EXAMPLE 16

Preparation of Compounds 38–66

Following the procedure of Examples 11–15, compounds 38–66 were prepared. The identity of these compounds, along with compounds 33–37, are summarized in Table 3 which includes the melting point of the compound as well as the examples in accordance of which the compound was synthesized.

TABLE 3

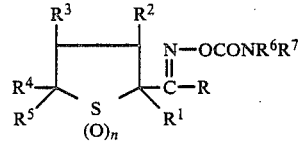

| Cpd. No. | n | R | $R^1$ | $R^2$ | $R^3$ | $R^4$ | $R^5$ | $R^6$ | $R^7$ | m.p. °C. | Made in accordance with Method of Ex. No. |
|---|---|---|---|---|---|---|---|---|---|---|---|
| 33 | 2 | $CH_3$ | H | H | H | H | H | $CH_3$ | H | 119–120 | 11 |
| 34 | 2 | 3-pyridyl | H | H | " | " | " | $CH_3$ | H | 154–165 | " |
| 35 | 2 | 3-pyridyl-HCl | H | H | " | " | " | $CH_3$ | H | tacky solid | 13 |
| 36 | 2 | $CH_3$ | H | H | " | " | " | $CH_3$ | $CH_3$ | 114–116° | 14 |
| 37 | 2 | $CH_2SO_2CH_3$ | H | H | " | " | " | $CH_3$ | H | 164–167 | 15 |
| 38 | 2 | $CH_3$ | $CH_3$ | H | " | " | " | $CH_3$ | H | 153–153.5 | 11 |
| 39 | 2 | $CH_3$ | H | H | " | " | " | $CH_2CH_3$ | H | oil | " |
| 40 | 2 | $CH_3$ | H | H | " | " | " | $(CH_2)_2CH_3$ | H | oil | " |
| 41 | 2 | $CH_3$ | H | H | " | " | " | $CH(CH_3)_2$ | H | 117–118 | " |
| 42 | 2 | $CH_3$ | H | H | " | " | " | $CH_2CH=CH_2$ | H | oil | " |
| 43 | 2 | $CH_3$ | H | H | " | " | " | $C(CH_3)_3$ | H | visc. oil | " |
| 44 | 2 | $CH_3$ | H | H | " | " | " | $(CH_2)_3CH_3$ | H | oil | " |
| 45 | 2 | $CH_3$ | H | H | " | " | " | $4-CH_3C_6H_4$ | H | 126–127 | " |
| 46 | 2 | $CH_2CH_3$ | H | H | " | " | " | $CH_3$ | H | 144–145 | " |
| 47 | 2 | $CH_2CH_3$ | H | H | " | " | " | $CH(CH_3)_2$ | H | visc. oil | " |
| 48 | 2 | $CH_2CH_3$ | H | H | " | " | " | $(CH_2)_3CH_3$ | H | visc. oil | " |
| 49 | 2 | $CH(CH_3)_2$ | H | H | " | " | " | $CH_3$ | H | 128–130 | " |
| 50 | 2 | $c-C_3H_5$ | H | H | " | " | " | $CH_3$ | H | 173–176 | " |
| 51 | 2 | $c-C_3H_5$ | H | H | " | " | " | $CH_3$ | H | visc. oil | " |
| 52 | 2 | $c-C_3H_5$ | H | H | " | " | " | $CH(CH_3)_2$ | H | visc. oil | " |
| 53 | 2 | $(CH_2)_3CH_3$ | H | H | " | " | " | $CH_3$ | H | 113–116° | " |
| 54 | 2 | $C(CH_3)_3$ | H | H | " | " | " | $CH(CH_3)_2$ | H | 178 dec* | " |
| 55 | 2 | $C(CH_3)_3$ | H | H | " | " | " | $(CH_2)_3CH_3$ | H | 160–161 | " |
| 56 | 2 | $CH_2SCH_3$ | H | H | " | " | " | $CH_3$ | H | glass | " |
| 57 | 2 | $CH_2CH_2SCH_3$ | H | H | " | " | " | $CH_3$ | H | 95–102 | " |
| 58 | 2 | $C_6H_5$ | H | H | " | " | " | $CH_3$ | H | 196 dec* | " |
| 59 | 2 | $C_6H_5$ | H | H | " | " | " | $CH(CH_3)_2$ | H | glass | " |
| 60 | 2 | $3-CH_3C_6H_4$ | H | H | " | " | " | $CH_3$ | H | 126–140 | " |
| 61 | 2 | $CH_2C_6H_5$ | H | H | " | " | " | $CH_3$ | H | 141–144 | " |
| 62 | 2 | 2-furyl | H | H | " | " | " | $CH_3$ | H | 189–191 dec* | " |
| 63 | 2 | 2-thienyl | H | H | " | " | " | $CH_3$ | H | 170–171 | " |
| 64 | 0 | $CH_3$ | H | H | " | " | " | $CH_3$ | H | 72 | " |
| 65 | 1 | $CH_3$ | H | H | " | " | " | $CH_3$ | H | oil | 15 |
| 66** | 2 | $CH_3$ | H | $CH_3$ | " | " | " | $CH_3$ | H | oil | 11 |
| 66a** | 2 | $CH_3$ | H | H | $CH_3$ | " | " | $CH_3$ | H | oil | " |

*Decomposing at that temperature
**Mixture thio)ethanone, O-[(methylamino)carbonyl]oxime (Compound 56) and 25 ml methylene chloride. The resultant reaction mixture was stirred at room temperature for 3 days. Thereafter, the reaction mixture was heated to reflux for one-half hour. The reaction mixture was cooled to 0° C. and filtered to remove m-chlorobenzoic acid. The filtrate was washed once with 5% sodium bicarbonate solution and dried over magnesium sulfate. Removal of the solvent under reduced pressure provided 1.8 g of a glassy foam. This crude product was purified on a preparative liquid chromatograph (Waters [trademark] Prep 500 A) using a silica column and eluting with 2:1 methylene chloride:acetone. The glassy solid (0.8 g) was treated with diethyl ether to give a white powder, 1-(tetrahydro-1,1-dioxo-2-thienyl)-2-

EXAMPLE 17

Preparation of 1-(tetrahydro-1,1-dioxo-2-thienyl-ethanone, O-(methylamine)-carbonyl)oxime (Compound 33)

To a stirred, cold (0° C.) solution of 10.1 g (0.1 mol) of triethylamine in 150 ml of tetrahydrofuran, (THF) 12 g (0.12 mol) of gaseous phosgene is added through a fitted glass tube. After the addition of the phosgene, 17.7 g (0.1 mol) of 1-(tetrahydro-1,1-thienyl)ethanone, oxime (compound 17) in 50 ml THF is added dropwise to the reaction mixture over a period of 30 minutes. The mixture maintained at 0° C., is stirred for 1 hour.

The reaction mixture is filtered to remove the triethylamine hydrochloride salt. The resultant filtrate is cooled to 0° C., and 10 g of gaseous methylamine is added over a period of 30 minutes. The reaction mixture is stirred for 1 hour. The methylamine hydrochloride salt is filtered. The filtrate is concentrated at a pressure of 20 mm Hg to give a viscous oil. The oil is crystallized from ethyl acetate to provide 1-(tetrahydro-1,1-dioxo-2-thienyl)-ethanone, O-[(methylamino)carbonyl]oxime.

EXAMPLE 18

Preparation of Formulations

The remaining examples relate to the pesticidal use of the compounds of this invention. In all these examples the compounds were diluted to one of the following concentrations: 6,000; 3,000; 1,000; 500; or 50 parts per million (ppm). To accomplish these dilutions, 0.6 g of the compound in question was dissolved in 10 ml of acetone to which were added 4 drops of a suitable wetting agent. This solution was further diluted with 100 ml of water to provide a 6,000 ppm suspension. In those instances where a 3,000 ppm concentration was used, an aliquot of the 6,000 ppm was further diluted to yield the 3,000 ppm suspension of the compound. In a similar manner the still more dilute suspensions of 1,000 ppm, 500 ppm and 50 ppm were prepared.

All the tests discussed below, which involved treatment with compounds of this invention at concentrations of 6,000; 3,000; 1,000; 500; and 50 ppm were always repeated with controls, in which the active compound was not provided, to permit a comparison upon which the percent control was calculated.

EXAMPLE 19

Control of Southern Corn Rootworm

Test formulations were prepared at 1000 and 500 ppm. Five ml of the dilution was pipetted onto a paper towel and inserted into a plastic bag. Two corn seedlings were also soaked in the chemical preparation and placed in the plastic bag. Bags were held for 18 hours before being loaded with 5 corn rootworm, *Diabrotica undecimpuntata*, larvae. After six days, the number of live larvae were noted and the percent control was calculated.

EXAMPLE 20

Control of Mites

Test compounds were prepared at 1000 ppm concentration. Cowpeas, in the first primary leaf stage, were used in the test. Two plants per pot (one primary leaf each) were used for each replicate; two replicates were used for each compound tested. The plants were sprayed with the dispersions using a spray atomizer to thoroughly drench the foliage.

One day following treatment, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves. On an estimated basis in comparison with the number of living mites on the control plants, the percent control was determined.

EXAMPLE 21

Control of Rice Planthopper

Test formulations of 1,000 ppm suspensions were prepared. Two rice seedling plants were treated with each formulation by spraying with a spray atomizer. Ten adult rice planthoppers, *Sogatodes oryzicola*, were placed on plants in each pot one day following treatment. The surviving planthoppers were counted after five days to determine the percent control.

EXAMPLE 22

Control of Tobacco Budworm

Suspensions of test formulations were prepared at 6,000 and 3,000 ppm. Two-tenths ml of the diluted formulation was pipetted onto the surface of 5 g of a synthetic diet mixture held in partially filled cells of a plastic jelly tray. Five cells were treated with the chemical dilution in this manner. Following treatment, a third instar larva of the tobacco budworm, *Heliothis virescens*, was placed in each cell. At the end of one and two weeks, trays were examined and the percent control was determined.

EXAMPLE 23

Control of Nematodes

Southern root-knot nematodes, *Meloidogyne incognita*, were reared in sandy culture soil using tomato as the host plant. Roots from culture plants were ground in a Waring blender. Ground roots and culture soils were mixed with equal parts of uninfested soil and the mixture was placed in pots. Test formulations were prepared at a concentration of 100 ppm. Twenty-five ml of the dilution drenched each pot, giving a resultant soil concentration of 50 ppm. An equal number of the pots were untreated with the compound. One day after treatment, two tomato seedlings were planted in each pot. Twelve days after planting, the soil was washed from the roots. The treatments were evaluated by comparing the number of knots on plant roots from treated soil to those from the untreated nematode-infested control.

The results of the above described tests are summarized Table 4.

TABLE 4

| | Percent Pesticidal Control | | | | |
|---|---|---|---|---|---|
| Cpd. No. | CR at 1000 ppm | MI at 1000 ppm | RPH at 1000 ppm | TB at 6000 ppm | NE at 50 ppm |
| 33 | 49 | 100 | 95** | 0 | 100 |
| 34 | 0 | 0 | 100 | 0* | 100 |
| 35 | 23** | 20 | 100 | 0* | 90 |
| 36 | 37 | 30 | 100 | 69 | 100 |
| 37 | 0** | 0 | 100 | 58* | 90 |
| 38 | 20 | 100 | 90 | 16 | 0 |
| 39 | 0 | 80 | 70 | 0 | 100 |
| 40 | 0 | 0 | 95 | 100 | 90 |
| 41 | 58 | 15 | 100 | 0 | 100 |
| 42 | 0 | 0 | 90 | 0* | 100 |
| 43 | 4 | 0 | 0 | 0 | 100 |
| 44 | 25 | 0 | 10 | 0 | 100 |
| 45 | 12 | 0 | 0 | 43 | 0 |
| 46 | 11 | 95 | 100 | 0 | 90 |
| 47 | 0 | 0 | 50 | 0 | 100 |
| 48 | 0 | 0 | 0 | 0 | 95 |
| 49 | 0 | 0 | 100 | 0 | 50 |
| 50 | 16 | 0 | 95 | 25 | 95 |
| 51 | 37 | 0 | 100 | 0 | 85 |
| 52 | 0 | 0 | 80 | 0 | 85 |
| 53 | 0 | 0 | 90 | 0 | 90 |
| 54 | 79 | 0 | 0 | 8 | 0 |
| 55 | 0 | 0 | 0 | 0 | 35 |

TABLE 4-continued

| Cpd. No. | CR at 1000 ppm | MI at 1000 ppm | RPH at 1000 ppm | TB at 6000 ppm | NE at 50 ppm |
|---|---|---|---|---|---|
| | | Percent Pesticidal Control | | | |
| 56 | 56** | 80 | 100 | 40* | 90 |
| 57 | 0 | 0 | 95 | 0 | 0 |
| 58 | 20 | 0 | 60 | 20 | 0 |
| 59 | 0 | 0 | 95 | 20 | 0 |
| 60 | 0 | 0 | 0 | 37* | 20 |
| 61 | 0 | 0 | 0 | 16 | 0 |
| 62 | 77 | 0 | 0 | 0* | 100 |
| 63 | 100 | 0 | 0 | 6* | 100 |
| 64 | 20** | 90 | 90 | 0* | 90 |
| 65 | 0** | 100 | 100 | 0 | — |

NOTES (for Table 4)
CR = Corn rootworm
MI = Mites
RPH = Rice plant hopper
TB = Tobacco budworm
NE = Nematodes
*at 3000 ppm concentration
**at 500 ppm concentration

EXAMPLE 23

Control of Rice Planthopper

To determine the systemic pesticidal effect of the instant compounds, 200 ppm suspensions formulations were prepared. These suspensions were prepared in accordance with the procedure enumerated in Example 17.

Thirty ml of the 200 ppm suspension was syringe injected under the root system of two rice seedling plants in a pot containing 600 grams of potting soil. The resulting soil concentration was 10 ppm. One day after treatment ten (10) adult rice planthoppers, *Sogatodes oryzicola*, were placed on plants and confined to the plants using a plastic cylinder. The surviving planthoppers were counted 5 days after loading to determine the percent control.

The results of this test are tabulated in Table 5.

TABLE 5

| Compound No. | Rate PPM | % Control of Planthoppers |
|---|---|---|
| 33 | 10 | 94 |
| 51 | 10 | 94 |
| 37 | 10 | 95 |
| 57 | 10 | 100 |

EXAMPLE 24

Control of Mites

Test formulations were prepared of a 900 ppm and a 225 ppm suspension in accordance with the procedure of Example 17.

Cotton plants in the first primary leaf stage were used in the test. Two plants per pot (one primary leaf each) were used for each replicate; two replicates were used for each compound tested. A 20 ml aliquot of the chemical preparation was watered on each of the pots containing 450 gm of soil. The resulting soil concentration for the 900 ppm suspension was 40 ppm; for the 225 ppm suspension it was 10 ppm. One day after treatment, a circle of tanglefoot was placed on the upper surface of the leaves and approximately 25 adult mites, *Tetranchus urticae*, were transferred into this confinement.

Six days following infestation with mites, the leaves were examined for live mites remaining on the leaves. On an estimated basis in comparison with the number of living mites on the control plants, the percent control was determined. The results are disclosed in Table 6 indicating systemic pesticidal activity.

TABLE 6

| Compound No. | Soil Concentration PPM | % Control of Mites |
|---|---|---|
| 33 | 40 | 100 |
| | 10 | 79 |

The preceding embodiments and examples will suggest other embodiments and examples to those skilled in the art. These other suggested embodiments and examples are within the contemplation of the present invention. Therefore, the present invention should be limited only by the appended claims.

What is claimed is:

1. A compound having the structural formula:

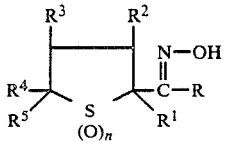

where R is $C_1$–$C_4$ alkyl, cyclopropyl, $C_2$–$C_4$ alkoxyalkyl, $C_2$–$C_4$ alkylthioalkyl, $C_2$–$C_4$ alkylsulfinylalkyl, $C_2$–$C_4$ alkylsulfonylalkyl, $C_4$–$C_8$ dialkylaminoalkyl, phenyl, $C_7$–$C_9$ aralkyl, $C_7$–$C_9$ alkaryl, furyl, thienyl or pyridyl; $R^1$ is hydrogen or $C_1$–$C_4$ alkyl; $R^2$, $R^3$, $R^4$ and $R^5$ are the same or different and are hydrogen or $C_1$–$C_4$ alkyl; and n is 0, 1 or 2.

2. A compound in accordance with claim 1 where R is $C_1$–$C_3$ alkyl, cyclopropyl, $C_2$–$C_3$ alkoxyalkyl, $C_3$–$C_4$ alkylthioalkyl, $C_3$–$C_4$ alkylsulfinylalkyl, $C_3$–$C_4$ alkylsulfonylalkyl, furyl, thienyl or pyridyl.

3. A compound in accordance with claim 1 where R is $C_1$–$C_2$ alkyl, cyclopropyl, methylthiomethyl, methylsulfonylmethyl, furyl, thienyl or pyridyl.

* * * * *